(12) United States Patent
Moctezuma

(10) Patent No.: US 6,306,126 B1
(45) Date of Patent: Oct. 23, 2001

(54) CALIBRATING DEVICE

(75) Inventor: José-Luis Moctezuma, Freiburg (DE)

(73) Assignee: Stryker Leibinger GmbH & Co KG, Freiburg (DE)

( * ) Notice: Subject to any disclaimer, the term of this patent is extended or adjusted under 35 U.S.C. 154(b) by 0 days.

(21) Appl. No.: 09/393,100

(22) Filed: Sep. 9, 1999

(30) Foreign Application Priority Data

Sep. 18, 1998 (DE) .............................................. 198 42 798

(51) Int. Cl.⁷ .................................................. A61B 17/00
(52) U.S. Cl. ............................ 606/1; 73/865.9; 73/1.75; 73/1.79; 73/1.01
(58) Field of Search ................................ 73/865.9, 1.01, 73/1.75, 1.79; 606/1

(56) References Cited

U.S. PATENT DOCUMENTS

| | | | | |
|---|---|---|---|---|
| 5,517,990 | * | 5/1996 | Kalfas et al. | 128/653.1 |
| 5,987,960 | * | 11/1999 | Messner et al. | 73/1.79 |
| 6,081,336 | * | 6/2000 | Messner et al. | 356/375 |

FOREIGN PATENT DOCUMENTS

| | | | | |
|---|---|---|---|---|
| 0832610-A2 | * | 1/1998 | (EP) | A61B/17/34 |
| 0 832 610 A2 | | 4/1998 | (EP) | A61B/17/34 |

OTHER PUBLICATIONS

Howmedica Leibinger GmbH, 1996, "Stereotactic Treatment Planning" brochure, pp. 1–20.
Hans F. Reinhardt, "Neuronavigation: A Ten–Year Review", The MIT Press (1996), pp. 329–341.
Carl Zeiss, "Experience New Perspectives–with the OPMI Neuro 200 System", pp. 1–12.

* cited by examiner

Primary Examiner—Linda C. M. Dvorak
Assistant Examiner—Jocelyn Debra Ram
(74) Attorney, Agent, or Firm—Pearne & Gordon LLP

(57) ABSTRACT

A calibrating device for detecting the position, firstly, of the axis of the shank (axis of action) and, secondly, of the front end (point of action or line of action) of a surgical instrument relative to an reference position determination device 42 mounted on the rear part of the instrument, has:

- two clamping-device carriers, each with a clamping device, in a clamping state the clamping devices bringing the shank of the instrument into a clearly defined clamped position;
- a supporting plate 12 on which the front end of the instrument rests in the clamped state; and
- a reference position determination device 42, the axis of action being essentially perpendicular to the supporting plate 12 in the clamped position, and the supporting plate and the reference position determination device 42 being connected firmly to one another.

59 Claims, 3 Drawing Sheets

CALIBRATING DEVICE

The present invention relates to a calibrating device for detecting the position, firstly, of the axis of the shank (axis of action) and, secondly, of the front end (point of action, line of action or area of action) of a surgical instrument relative to an emitter mounted on the instrument.

Modern imaging methods such as x-ray tomography and nuclear magnetic resonance are nowadays an important aid in surgery. It is particularly helpful if the surgical instruments used together with the image of the patient can be shown on a screen during surgical interventions. For this purpose, the position of the surgical instruments relative to the patient must be measured continuously during the operation.

One conventional method is to use a stereotactic frame. The stereotactic frame is attached firmly to the patient and the surgical instruments are secured on the frame, allowing their position relative to the patient to be determined in a simple manner. There is a description of stereotactic frames in the brochure "Stereotactic Treatment Planning" issued by Howmedica Leibinger GmbH in 1996. There is a survey of various systems in the article entitled "Neuronavigation: A ten-year review" by Hans F. Reinhardt in the book "Computer-integrated surgery" by R. H. Taylor, S. Lavallee; G. C. Burdea, R. Mosges; Cambridge/Mass., London/England: The MIT Press (1966), Page 329ff.

However, attaching a stereotactic frame to the patient is very involved and unpleasant for the patient.

In more modern systems, therefore, the position of a surgical instrument is measured by infrared radiation ("navigator"). In this method, the position of the patient and the position of the surgical instrument are determined separately and then correlated. A system of this kind is shown, for example, in the brochure entitled "Experience new perspectives—with the OPM® Neuro 200 system", Carl Zeiss, D-73446 Oberkochen.

The position of the patient is measured as follows: four screws, for example, provided with marking balls containing a contrast agent are first of all inserted into the patient. These marking balls can be seen on a CT recording and can thus serve as a reference point. During the operation, the marking balls are then removed, and a so-called navigation pointer is inserted at precisely the correct location into a remaining hollow. The navigation pointer has infrared LEDs, the radiation of which is recorded by a CCD camera situated, for example, over the operating table. Since a plurality of diodes are emitting radiation simultaneously, the system can calculate the position of the tip of the navigation pointer and hence the position of the hollow. If this method is carried out for all four screws, four points on the patient are associated with a clearly defined spatial position, it being possible for the system to calculate the spatial position of the patient from just three points, the fourth point acting as a control point.

The position of the surgical instrument is determined in a similar manner with infrared radiation. An emitter having LEDs, the position of which in space can be calculated by means of the data supplied by the CCD camera, is mounted on the rear part of the surgical instrument (e.g behind the handle). If the computer system knows the position of the tip of the instrument relative to the emitter, it can likewise calculate the position of the tip of the instrument in space (or of some other point of action) and the instrument can be shown on the computer screen together with the CT image. Since the emitter is connected firmly to the surgical instrument, the position of the tip of the instrument relative to the emitter need only be determined once, and the corresponding data are input into the computer system. However, calibration in this way has hitherto been very involved since it cannot be performed by the surgeon himself.

It would be desirable for the surgeon to be able to connect a wide variety of surgical instruments firmly to an emitter before or during an operation and to be able to quickly perform the calibration himself. Hitherto, there have been no methods for such calibration because surgical instruments have a very wide variety of shapes. In particular, not all surgical instruments have a tip (point of action). The end of the instrument can, for example, also be an edge (line of action), as in the case of a chisel, or be spoon-shaped. In the case of a tube, the end of the instrument has an area of action. Another difficulty in ascertaining the end of the instrument is that the axis of the shank of the instrument, i.e. the axis of action, which can, for example, be an axis of rotation, may be bent relative to the rear part of the instrument. A surgical instrument of this kind, with a bent shape, is particularly difficult to calibrate. It would therefore be desirable if it were also possible to determine the position of the axis of action during calibration.

EP 0 832 610 A2 describes a calibrating device for determining the position both of the axis of a shank and of the end of a surgical instrument relative to an emitter mounted in the latter. In this case, the distance between the area of action of the instrument and a reference surface is determined by a method in which the reference surface is touched by the tip of the instrument.

It is therefore the object of the invention to provide a calibrating device for determining the position, firstly, of the axis of the shank (axis of action) and, secondly, of the front end of the instrument (point of action, line of action or area of action) of a surgical instrument relative to an emitter mounted on the rear part of the instrument, which device is simple and quick to operate.

The distinguishing features of the calibrating device according to the invention are given in the patent claims.

The calibrating device preferably has: two clamping-device carriers, each with a clamping device, in a clamped state the clamping devices bringing the shank of the instrument into a clearly defined clamped position relative to the calibrating device; a supporting plate on which the front end of the instrument rests in the clamped state; and a reference emitter, the axis of action of the instrument being essentially perpendicular to the supporting plate in the clamped position, and the supporting plate and the reference emitter of the calibrating device being connected firmly to one another.

The calibrating device according to the invention has the advantage that it can be operated in situ by the surgeon himself. All that is required is to mount an emitter on the instrument and then bring the instrument into the clamped position in the calibrating device, i.e. the front end of the instrument is resting on the supporting plate and the clamping devices are clamping the shank of the instrument so that the axis of the shank is perpendicular to the supporting plate, more specifically colinear with a calibrating-device axis defined by the clamping devices. The CCD camera now determines both the position of the emitter and the position of the reference emitter of the calibrating device and can thus acquire the position of the axis of the shank and of the end of the instrument relative to the emitter of the instrument. The position of the end of the instrument is determined insofar as the plane in which the end of the instrument lies is calculated.

Preferably, at least one clamping-device carrier can be displaced in the direction perpendicular to the supporting plate. This makes the calibration system more adaptable to different surgical instruments with shanks of different lengths.

Preferably, the supporting plate is arranged on a base plate and four columns extending perpendicular to the supporting plate are attached to the base plate at the corners of a quadrilateral, each clamping-device carrier being fixed to at least one column. The use of a base plate has the advantage that the entire system is made more stable. The columns also help in this respect.

Preferably, the clamping-device carriers are each designed as a plate which has four guide holes for guidance along the columns and a through-opening in the center for the surgical instrument. This stabilizes the position of the clamping-device carriers, contributing to the precision of the calibrating device.

The plates preferably have guide sleeves for external guidance along the columns, and a stop is provided at the end of the columns, thus preventing the plates from being pushed beyond the columns and out of the system.

The fastening of the plates is improved by locking screws, by means of which they are held fast in a particular position on the column.

In an advantageous embodiment, the clamping devices each have a through-opening for the surgical instrument and at least three gripping jaws, which leave the opening at least partially free in an open position and close it, preferably completely, in a closed position. In the open position, the surgical instrument can be inserted into the calibrating device. The three gripping jaws are then moved into the clamping position, which is a position between the open position and the closed position. Those surfaces of the gripping jaws which enter into engagement with the surgical instrument are at the same radial distance from the above-mentioned axis of the calibrating device; they therefore define this axis.

It is advantageous if the gripping jaws have pins and the clamping devices each have a slotted disk with guide slots for each pin of the gripping jaws in the clamping device. The gripping jaws are moved and brought from the open position into the clamping position or the closed position and vice versa simply by turning the slotted disk, by means of a turning arm for example.

The reference position determination device preferably comprises two supports with emitters which are attached firmly to the base plate, parallel to the columns. This too contributes to a stabilization of the system and hence also to increase the precision of calibration.

It is advantageous if each support has at least two emitters and the emitters are infrared LEDs. The use of a total of at least four LEDs allows the position of the calibrating device in three-dimensional space to be determined precisely from the measured values for three LEDs, and the fourth LED is used as a control for the measurement and calculation.

It is desirable not only to determine the plane in which the line of action, i.e. the edge of a chisel, or the area of action, i.e. the area surrounded by a tube, lies but also to determine how wide the line of action is or how large the area of action is. For this purpose, an L-shaped measuring angle can be attached to the calibrating device, this being explained in greater detail below.

It is advantageous, for checking the data obtained during calibration, if a shaped body, preferably a ball, is firmly connected to the calibrating device.

Preferred embodiments are described with reference to the drawings, in which.

Figure 1:
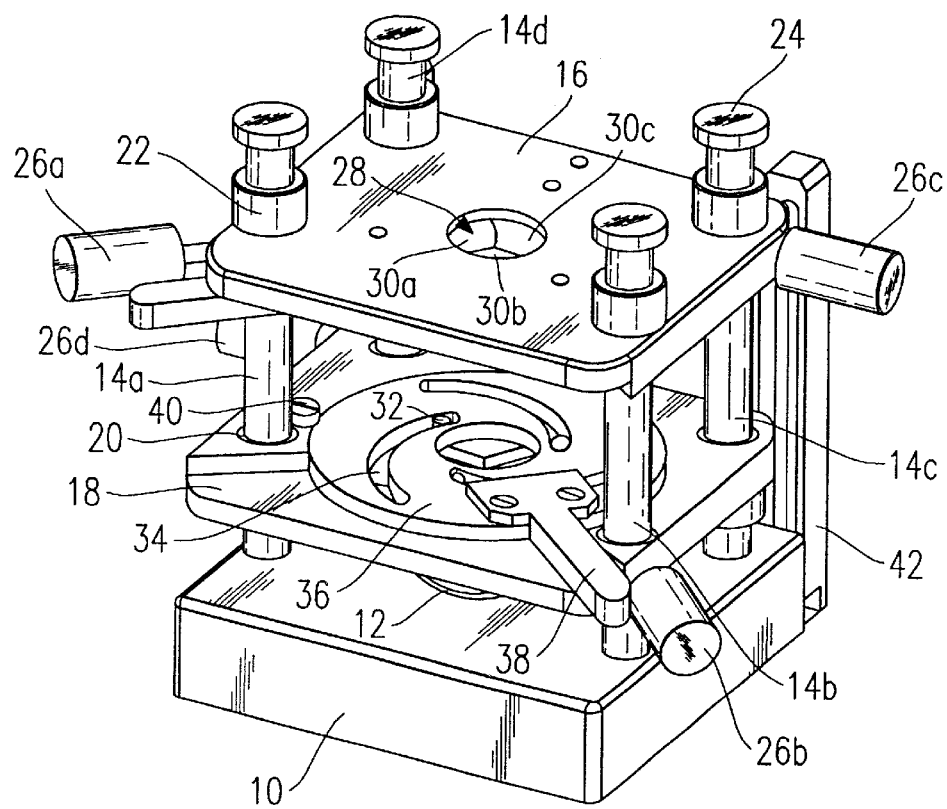
FIG. 1 is a perspective front view of a calibrating device in accordance with the invention.

A supporting plate 12 is arranged on a thick, heavy base plate 10. Four columns 14a, 14b, 14c, 14d extending perpendicular to the supporting plate and hence also perpendicular to the base are mounted on the base plate at the corners of a quadrilateral. An upper plate 16 and a lower plate 18 can be moved in a sliding manner on the columns 14a–d. The two plates 16 and 18 are of identical construction and are merely arranged reversed in the calibrating device. For this reason, components of plates 16 and 18 will only be provided with reference numerals on one of the two plates.

Each plate has four guide holes 20 for guidance along the columns, and guide sleeves 22 which improve guidance. At the end of each of the columns is a stop 24, preventing the plates from being removed from the calibrating device, even accidentally. Locking screws 26a, 26b, 26c and 26d are provided for fastening the plates, the upper plate 16 being held by locking screws 26a and 26c, and the lower plate being held by locking screws 26b and 26d.

The plates 16 and 18 each have a through-opening 28 in the center for the surgical instrument.

Figure 3:
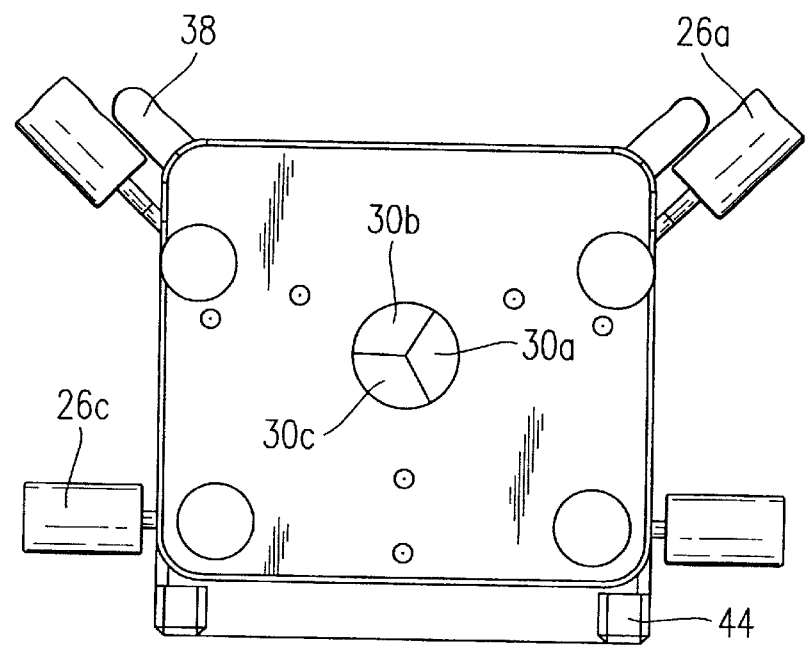
FIG. 3 is a plan view of the calibrating device in FIG. 1.

A surgical instrument is clamped in a clamping device, the actual clamping device comprising three gripping jaws 30a, 30b, 30c which, in an open position, leave the opening 28 at least partially free and, in a closed position, as shown, for example, in FIG. 3, completely close the said opening. The gripping jaws 30a–30c are each provided with pins 32, each of these being guided in a guide slot 34 in a slotted disk 36. The slotted disk 36 is actuated by turning a turning arm 38. They are each secured to the plates by screws 40.

To enable the position of the calibrating device to be recorded by a CCD camera, a U-shaped reference emitter 42 with two supports 44, which is firmly connected to the base plate 10, is provided on the calibrating device, the two supports 44 extending parallel to the columns 14a–d. Each support 44 has two infrared LEDs 46 as emitters.

The components of the calibrating device are composed almost exclusively of metal and are machined to a high accuracy. The supporting plate 12, for example, is finely polished, the gripping jaws 30a–c close with a high degree of accuracy, and the individual components are connected to one another in an accurately adjusted manner. An adjusting pin 48 is used for adjusting the reference emitter on the base plate 10, for example. Screws 50 are provided for actually retaining it.

If calibration is to be performed for a particular surgical instrument, an emitter must first be mounted in a fixed manner on the instrument. The gripping jaws 30a–c of the two plates 16 and 18 are each moved into an open position by turning the turning arms 38 in an appropriate manner. The surgical instrument can then be passed through the openings 28 until its front end comes to rest on the supporting plate 12. Depending on the length of the shank, the plates 16 and 18 can now be adjusted in such a way that the distance between them is at a maximum. The minimum distance should be 2 cm. This can also be enforced by building in a spacing member. Such a spacing member could, for example, have a shape similar to that of the guide sleeve 22 and would have to be attached in an appropriate manner to the underside of plate 16 or the upper side of plate 18. When moving the plates, the locking screws are first of all loosened, after which the plate is displaced and the locking screws are then re-tightened.

If the upper plate 16 and the lower plate 18 are in a favorable position corresponding to the shape of the shank of the surgical instrument, the turning arms 38 are actuated and the surgical instrument is hence clamped fast. The shape of the gripping jaws ensures that the shank of the instrument takes up a precisely defined clamped position in which the axis of action, i.e. the axis of the shank, is essentially perpendicular to the supporting plate 12. The computer software now compares the signal received by the CCD camera from the emitter mounted on the instrument with the reference emitter 42 of the calibrating device. In this way, the software can calculate both the position of the plane in which the front end of the instrument (point of action or line of action) is located relative to the position of the emitter and the position of the axis of the shank, the axis of action. This is even possible, in particular, in the case of curved instruments on which the rear part of the instrument bends away from the axis of action. Overall, it is possible to calibrate about 95% of all conventional surgical instruments with the calibrating device.

The calibrating data are then fed to the operation software, and the operation software can then deduce the position of the axis of action and of the front end of the instrument by acquiring the position of the emitter.

Figure 2:
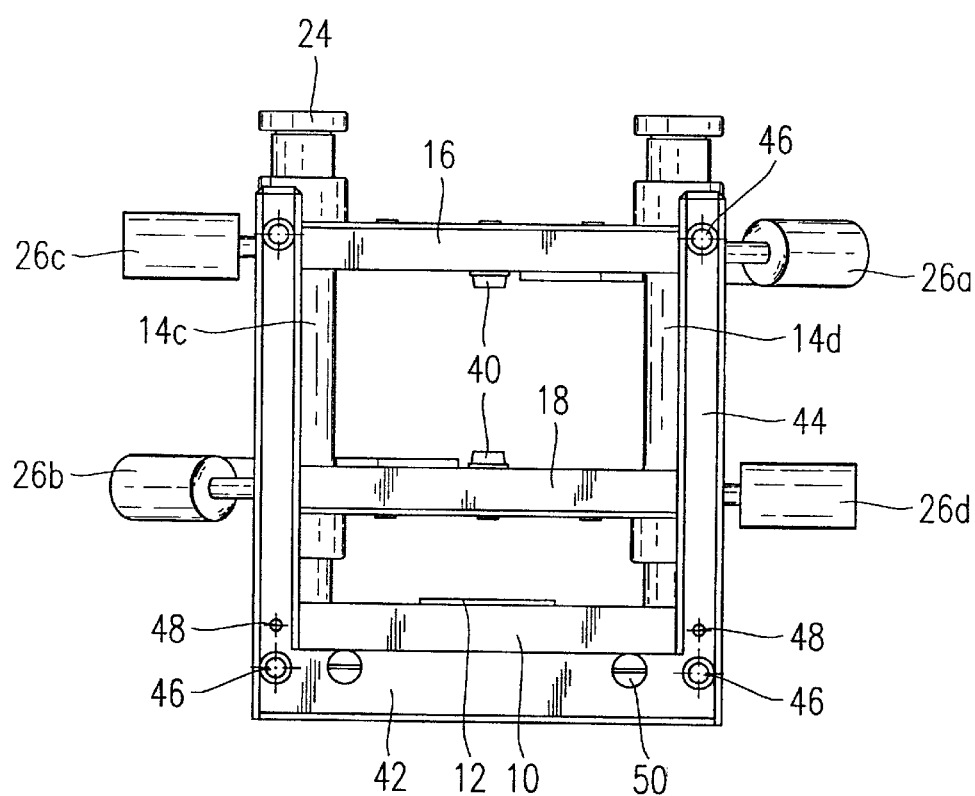
FIG. 2 is a rear view of the calibrating device shown in FIG. 1.
Figure 4:
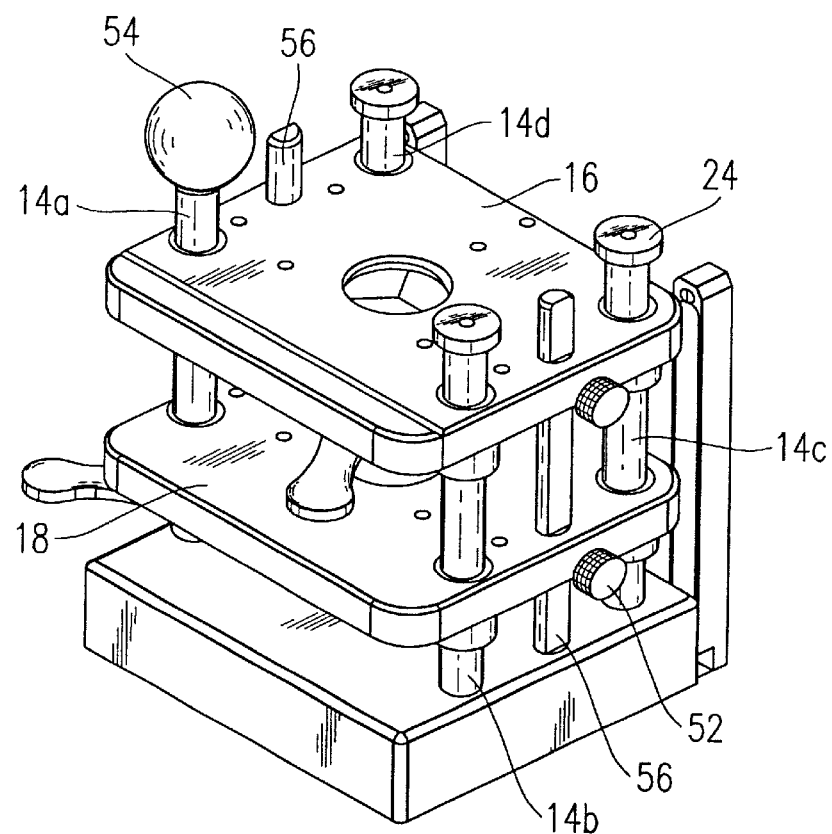
FIG. 4 is a perspective view of an alternative embodiment of a calibrating device.

In addition to the columns 14a–14d, the alternative embodiment shown in FIG. 4 has two guide rods 56, to which the plates 16 and 18 are fastened by means of locking screws 52. This symmetrical arrangement of the locking screws 52 increases stability as compared with the arrangement of the locking screws 26a–d which is shown in FIGS. 1 to 3.

The alternative embodiment furthermore has a shaped body 54 on the column 14a instead of the stop 24. In the embodiment example shown, this shaped body is spherical. This shaped body allows the data obtained during calibration to be checked. With the display unit switched on, the shaped body is sensed with the front end of the instrument. The computer software then compares the position and shape of the shaped body, i.e. the ball 54, which are known to it, with the position obtained by calculation using the calibration data. This enables the latter to be checked.

The calibrating station described above provides information on the exact position of the axis of action of a surgical instrument relative to the emitter and on the plane in which the end of the instrument is located. However, there is no further information on the end of the instrument. It would be desirable, particularly in the case of instruments whose end has a known shape, to obtain information on the dimensions of the end of the instrument as well. It would be useful, for example, to acquire information on the width of the line of action of a chisel or the diameter of a tube.

Figure 5:
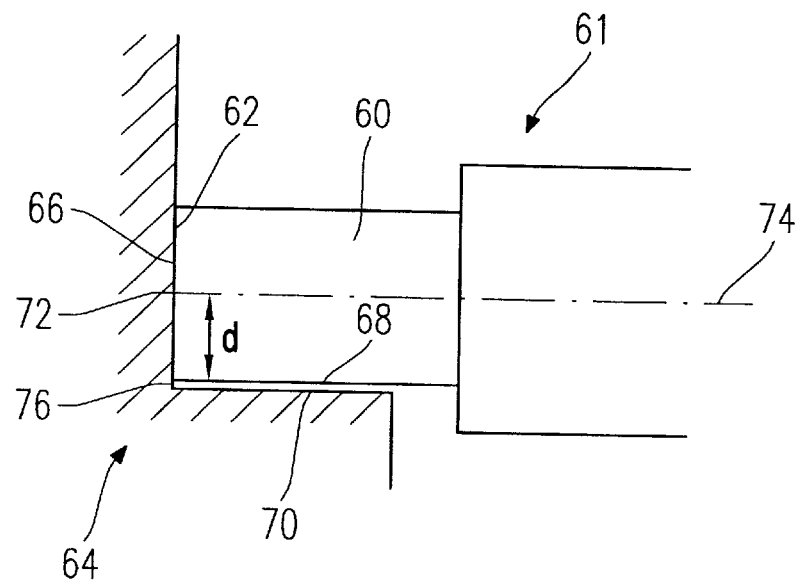
FIG. 5 shows schematically how the length of the line of action of a chisel is determined.

For this purpose, a suitable geometrical body can likewise be mounted on the calibrating device. The simplest body of this kind is an L-shaped measuring angle which is firmly connected to the calibrating device. It can, for example, be attached to the upper plate 16. Connecting it firmly to the calibrating device allows the exact position and line of the angle to be determined on the basis of the infrared radiation emitted by the reference emitter. FIG. 5 shows how the front part 60 of a chisel 61 is introduced into an angle 64 and, more specifically, the end of the instrument, the line of action 62, meets the surface 66 of the L-shaped measuring angle 64, while side 68 of the front part 60 of the chisel touches surface 70 of the L-shaped measuring angle edge 64. (It is only for drawing reasons that a small gap has been shown between surfaces 68 and 70).

Based on data already known from the previously performed calibration, the point 72 at which the axis of action 74 touches surface 66 can now be calculated. The distance d between this point 72 and the corner 76 of the L-shaped measuring angle 64 corresponds precisely to half the width of the line of action of the chisel 61. Assuming a symmetrical chisel, the software can thus calculate the width of the line of action.

Figure 6:
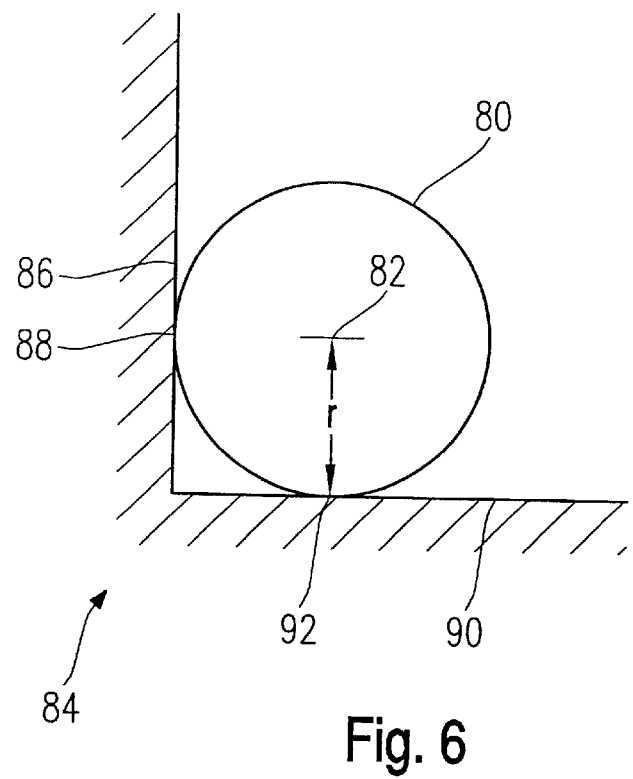
FIG. 6 shows schematically how the radius of a tube is determined.

The measurement of the radius and hence the measurement of the area of action of a surgical instrument with a tubular front part is performed in a similar manner. This is shown schematically by means of FIG. 6. In contrast to FIG. 5, the axis of action of the instrument in FIG. 6 points perpendicularly out of the plane of the drawing. FIG. 6 shows the circular periphery 80 of the front end of the instrument. The axis of action passes through the point 82. The instrument is inserted vertically from above into the L-shaped measuring angle 84 and thus touches side 86 of the L-shaped measuring angle 84 at the point 88 and side 90 of the L-shaped measuring angle at the point 92. The distance r between the point 82 and the point 92 can now be calculated by the software, which, of course, knows the course of side 90 of the angle from the outset. During measurement, infrared radiation is then emitted by the emitter on the surgical instrument and the software can determine the point 82 and hence also the distance r. As an alternative to or simultaneously with this check, it is also possible for the distance between the point 82 and the point 88 to be calculated.

In the embodiment examples of the invention described above, an emitter 42 is used as a reference position determination device. The emitter uses LEDs. However, it is also possible to provide other instruments as the reference position determination device and to use other physical principles of action, such as mechanical, electromechanical, acoustic or magnetic principles of action, for location (position determination). Numerous modifications of the calibrating device described are possible. For example, the reference position determination device or reference position determination devices can also be attached to the calibrating device at a different point. It is also possible to use a spring structure instead of the gripping jaws or a design such as that used in drill chucks. Instead of the plates 16 and 18, it would also be possible to use different clamping-device carriers, such as a sturdy grid. A cuboid or a pyramid can be used instead of a ball as the shaped body.

What is claimed is:

1. A calibrating device for detecting the position of an axis of a shank of a surgical instrument and of a front end of said surgical instrument relative to a first reference position determination device mounted on the instrument, comprising: two clamping-device carriers, each with a clamping device, defining a clamping state when the clamping devices bring the shank of the instrument into a clearly defined clamped position relative to the calibrating device; a supporting plate (12) adapted to enable the front end of the instrument to rest on the plate when the instrument is in the clamped position; and a second reference position determination device (42), wherein the axis of the shank is essentially perpendicular to the supporting plate (12) when the instrument is in the clamped position, the supporting plate (12) and the second reference position determination device are connected firmly to one another, and at least one clamping-device carrier can be displaced in a direction perpendicular to the supporting plate.

2. The calibrating device as claimed in claim 1, wherein the first reference position determination device is an emitter.

3. The calibrating device as claimed in claim 1, wherein the first reference position determination device acts mechanically, electromechanically, acoustically or magnetically.

4. The calibrating device as claimed in claim 1, wherein the supporting plate (12) is arranged on a base plate (10), and wherein four columns (14a–d) extending perpendicular to the supporting plate are attached to the base plate at the corners of a quadrilateral, each clamping-device carrier being fixed to at least one column.

5. The calibrating device as claimed in claim 4, wherein the clamping-device carriers are each designed as a plate (16, 18) which has four guide holes (22) for guidance along the columns and a through-opening (28) in the center, said through-opening (28) being adapted to hold the surgical instrument.

6. The calibrating device as claimed in claim 5, wherein the plates have guide sleeves (24) for guidance along the columns (14a–d), and wherein a stop (24) is provided at the end of the columns.

7. The calibrating device as claimed in claim 5, wherein the plates (16, 18) have locking screws (26a–d) by means of which they are held fast in a particular position on the column (14a–d).

8. The calibrating device as claimed in claim 1, wherein the clamping devices each have a through-opening (28) adapted to hold the surgical instrument and at least three gripping jaws (30a–c), which leave the opening (28) at least partially free in an open position and close it completely, in a closed position.

9. The calibrating device as claimed in claim 8, wherein the gripping jaws (30a–c) have pins (32) and the clamping devices each have a slotted disk (36) with guide slots (34) for each pin (32) of the gripping jaws (30a–c) in the clamping device.

10. The calibrating device as claimed in claim 1, wherein the supporting plate (12) is arranged on a base plate (10) and wherein the second reference position determination device (42) comprises two supports (44) with emitters (46) which are attached firmly to the base plate (10), said supports (44) being parallel to the columns (14a–d).

11. The calibrating device as claimed in claim 10, wherein each support (44) has at least two emitters.

12. The calibrating device as claimed in claim 11, wherein the emitters are infrared LEDs (46).

13. The calibrating device as claimed in claim 1, further comprising a measuring angle.

14. The calibrating device as claimed in claim 1, further comprising a shaped body.

15. A calibrating device for detecting the position of an axis of a shank of a surgical instrument and of a front end of said surgical instrument relative to a first reference position determination device mounted on the instrument, comprising: two clamping-device carriers, each with a clamping device, defining a clamping state when the clamping devices bring the shank of the instrument into a clearly defined clamped position relative to the calibrating device; a supporting plate (12) adapted to enable the front end of the instrument to rest on the plate when the instrument is in the clamped position, said supporting plate (12) being arranged on a base plate (10), and wherein four columns (14a–d) extending perpendicular to the supporting plate are attached to the base plate at the corners of a quadrilateral, each clamping-device carrier being fixed to at least one column; and a second reference position determination device (42), wherein the axis of the shank is essentially perpendicular to the supporting plate (12) when the instrument is in the clamped position, and the supporting plate (12) and the second reference position determination device are connected firmly to one another.

16. The calibrating device as claimed in claim 15, wherein the first reference position determination device is an emitter.

17. The calibrating device as claimed in claim 15, wherein the first reference position determination device acts mechanically, electromechanically, acoustically or magnetically.

18. The calibrating device as claimed in claim 15, wherein the clamping-device carriers are each designed as a plate (16, 18) which has four guide holes (22) for guidance along the columns and a through-opening (28) in the center, said through-opening (28) being adapted to hold the surgical instrument.

19. The calibrating device as claimed in claim 18, wherein the plates have guide sleeves (24) for guidance along the columns (14a–d), and wherein a stop (24) is provided at the end of the columns.

20. The calibrating device as claimed in claim 18, wherein the plates (16, 18) have locking screws (26a–d) by means of which they are held fast in a particular position on the column (14a–d).

21. The calibrating device as claimed in claim 15, wherein the clamping devices each have a through-opening (28) adapted to hold the surgical instrument and at least three gripping jaws (30a–c), which leave the opening (28) at least partially free in an open position and close it, preferably completely, in a closed position.

22. The calibrating device as claimed in claim 21, wherein the gripping jaws (30a–c) have pins (32) and the clamping devices each have a slotted disk (36) with guide slots (34) for each pin (32) of the gripping jaws (30a–c).

23. The calibrating device as claimed in claim 22, wherein the slotted disk (36) can be turned by means of a turning arm (38).

24. The calibrating device as claimed in claim 15, wherein the supporting plate (12) is arranged on a base plate (10) and wherein the second reference position determination device (42) comprises two supports (44) with emitters (46) which are attached firmly to the base plate (10), said supports (44) being parallel to the columns (14a–d).

25. The calibrating device as claimed in claim 24, wherein each support (44) has at least two emitters.

26. The calibrating device as claimed in claim 25, wherein the emitters are infrared LEDs (46).

27. The calibrating device as claimed in claim 15, further comprising a measuring angle.

28. The calibrating device as claimed in claim 15, further comprising a shaped body.

29. A calibrating device for detecting the position of an axis of a shank of a surgical instrument and of a front end of said surgical instrument relative to a first reference position determination device mounted on the instrument, comprising: at least one clamping device for clamping the instrument in a clearly defined clamped position relative to the calibrating device, each clamping device having a through-opening (28) adapted to hold the surgical instrument and at least three gripping jaws (30a–c), which leave the opening at least partially free in an open and close it completely in a closed position; a supporting plate (12) adapted to enable the front end of the instrument to rest on the plate when the instrument is in the clamped position; and a second reference position determination device (42), wherein the axis of the shank is essentially perpendicular to the supporting plate (12) when the instrument is in the clamped position, and the supporting plate (12) and the second reference position determination device are connected firmly to one another.

30. The calibrating device as claimed in claim 29, wherein the first reference position determination device is an emitter.

31. The calibrating device as claimed in claim 29, wherein the first reference position determination device acts mechanically, electromechanically, acoustically or magnetically.

32. The calibrating device as claimed in claim 29, further comprising two clamping-device carriers, each with one of said at least one clamping device, defining a clamping state when the clamping devices bring the shank of the instrument into the clearly defined clamped position relative to the calibrating device.

33. The calibrating device as claimed in claim 32, wherein the supporting plate (12) is arranged on a base plate (10), and wherein four columns (14a–d) extending perpendicular to the supporting plate are attached to the base plate at the corners of a quadrilateral, each clamping-device carrier being fixed to at least one column, and wherein the clamping-device carriers are each designed as a plate (16, 18) which has four guide holes (22) for guidance along the columns and said through-opening (28) in the center, and said through-opening (28) being arranged in the center of said plate.

34. The calibrating device as claimed in claim 31, wherein the plates have guide sleeves (24) for guidance along the columns (14a–d), and wherein a stop (24) is provided at the end of the columns.

35. The calibrating device as claimed in claim 31, wherein the plates (16, 18) have locking screws (26a–d) by means of which they are held fast in a particular position on the column (14a–d).

36. The calibrating device as claimed in claim 29, wherein the gripping jaws (30a–c) have pins (32) and the clamping devices each have a slotted disk (36) with guide slots (34) for each pin (32) of the gripping jaws (30a–c) in the clamping device.

37. The calibrating device as claimed in claim 36, wherein the slotted disk (36) can be turned by means of a turning arm (38).

38. The calibrating device as claimed in claim 29, wherein the supporting plate (12) is arranged on a base plate (10) and wherein the second reference position determination device (42) comprises two supports (44) with emitters (46) which are attached firmly to the base plate (10), said supports (44) being parallel to the columns (14a–d).

39. The calibrating device as claimed in claim 38, wherein each support (44) has at least two emitters.

40. The calibrating device as claimed in claim 39, wherein the emitters are infrared LEDs (46).

41. The calibrating device as claimed in claim 29, further comprising a measuring angle.

42. The calibrating device as claimed in claim 29, further comprising a shaped body.

43. A calibrating device for detecting the position of an axis of a shank of a surgical instrument and of a front end of said surgical instrument relative to a first reference position determination device mounted on the instrument, comprising: at least one clamping device for clamping the instrument in a clearly defined clamped position relative to the calibrating device; a supporting plate (12) adapted to enable the front end of the instrument to rest on the plate when the instrument is in the clamped position; and a second reference position determination device (42), wherein the axis of the shank is essentially perpendicular to the supporting plate (12) when the instrument is in the clamped position, and the supporting plate (12) and the second reference position determination device are connected firmly to one another, wherein the supporting plate (12) is arranged on a base plate (10)) and wherein the second reference position determination device (42) comprises two supports (44) with emitters (46) which are attached firmly to the base plate (10), said supports (44) being parallel to the columns (14a–d).

44. The calibrating device as claimed in claim 43, wherein the first reference position determination device is an emitter.

45. The calibrating device as claimed in claim 43, wherein the first reference position determination device acts mechanically, electromechanically, acoustically or magnetically.

46. The calibrating device as claimed in claim 43, further comprising two clamping-device carriers, each with one of said at least one clamping device, defining a clamping state when the clamping devices bring the shank of the instrument into the clearly defined clamped position relative to the calibrating device.

47. The calibrating device as claimed in claim 46, wherein the supporting plate (12) is arranged on a base plate (10), and wherein four columns (14a–d) extending perpendicular to the supporting plate are attached to the base plate at the corners of a quadrilateral, each clamping-device carrier being fixed to at least one column, and wherein the clamping-device carriers are each designed as a plate (16, 18) which has four guide holes (22) for guidance along the columns and a through-opening (28) in the center, said through-opening (28) being adapted to the surgical instrument.

48. The calibrating device as claimed in claim 47, wherein the plates have guide sleeves (24) for guidance along the columns (14a–d), and wherein a stop (24) is provided at the end of the columns.

49. The calibrating device as claimed in claim 47, wherein the plates (16, 18) have locking screws (26a–d) by means of which they are held fast in a particular position on the column (14a–d).

50. The calibrating device as claimed in claim 43, wherein the clamping devices each have a through-opening (28) adapted to hold the surgical instrument and at least three gripping jaws (30a–c), which leave the opening (28) at least partially free in an open position and close it in a closed position, and wherein the gripping jaws (30a–c) have pins (32) and the clamping devices each have a slotted disk (36) with guide slots (34) for each pin (32) of the gripping jaws (30a–c).

51. The calibrating device as claimed in claim 50, wherein the slotted disk (36) can be turned by means of a turning arm (38).

52. The calibrating device as claimed in claim 43, wherein each support (44) has at least two emitters.

53. The calibrating device as claimed in claim 52, wherein the emitters are infrared LEDs (46).

54. The calibrating device as claimed in claim 43, further comprising a measuring angle.

55. The calibrating device as claimed in claim 43, further comprising a shaped body.

56. A calibrating device for detecting the position of an axis of a shank of a surgical instrument and of a front end of said surgical instrument relative to a first reference position determination device mounted on the instrument, comprising: at least one clamping device for clamping the instrument in a clearly defined clamped position relative to the calibrating device; a supporting plate (12) adapted to enable the front end of the instrument to rest on the plate when the instrument is in the clamped position; and a second reference position determination device (42), wherein the axis of the shank is essentially perpendicular to the supporting plate (12) when the instrument is in the clamped position, and the supporting plate (12) and the second reference position determination device are connected firmly to one another, wherein said calibration device further comprises at least one of a measuring angle or a ball.

57. The calibrating device as claimed in claim 56, wherein the first reference position determination device is an emitter.

58. The calibrating device as claimed in claim 56, wherein the first reference position determination device acts mechanically, electromechanically, acoustically or magnetically.

59. The calibrating device as claimed in claim 56, further comprising two clamping-device carriers, each with one of said at least one clamping device, defining a clamping state when the clamping devices bring the shank of the instrument into the clearly defined clamped position relative to the calibrating device.

* * * * *

UNITED STATES PATENT AND TRADEMARK OFFICE
CERTIFICATE OF CORRECTION

PATENT NO. : 6,306,126 B1
DATED : October 23, 2001
INVENTOR(S) : Jose-Luis Moctezuma It is certified that error appears in the above-identified patent and that said Letters Patent is hereby corrected as shown below:

Column 9,
Lines 36 and 40, delete "claim 31" and insert -- claim 33 --.

Signed and Sealed this

Fourteenth Day of May, 2002

Attest:

JAMES E. ROGAN
*Attesting Officer*   *Director of the United States Patent and Trademark Office*